United States Patent
Cook et al.

(10) Patent No.: US 7,081,132 B2
(45) Date of Patent: Jul. 25, 2006

(54) FLEXIBLE BARB FOR ANCHORING A PROSTHESIS

(75) Inventors: William A. Cook, Bloomington, IN (US); Michael P. DeBruyne, Bloomington, IN (US); Benjamin Nickless, Bloomington, IN (US); Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 157 days.

(21) Appl. No.: 10/431,809

(22) Filed: May 8, 2003

(65) Prior Publication Data

US 2003/0236570 A1  Dec. 25, 2003

Related U.S. Application Data

(60) Provisional application No. 60/381,046, filed on May 16, 2002.

(51) Int. Cl.
*A61F 2/06* (2006.01)
(52) U.S. Cl. ..................................... 623/1.36
(58) Field of Classification Search ...... 623/1.13–1.15, 623/1.36, 13.14; 606/153–155, 75, 151
See application file for complete search history.

(56) References Cited

U.S. PATENT DOCUMENTS

| 5,387,235 A | 2/1995 | Chuter |
| 5,527,355 A | 6/1996 | Ahn |
| 5,693,084 A | 12/1997 | Chuter |
| 5,707,388 A | 1/1998 | Lauterjung |
| 5,843,167 A | 12/1998 | Dwyer et al. |
| 5,921,995 A | 7/1999 | Kleshinski |
| 5,961,546 A | 10/1999 | Robinson et al. |
| 6,004,347 A | 12/1999 | McNamara et al. |
| 6,200,336 B1 | 3/2001 | Pavcnik et al. |
| 6,214,025 B1 | 4/2001 | Thistle et al. |
| 6,221,102 B1 | 4/2001 | Baker et al. |
| 6,322,587 B1 | 11/2001 | Quiachon et al. |
| 6,355,056 B1 | 3/2002 | Pinheiro |
| 6,355,061 B1 | 3/2002 | Quiachon et al. |

FOREIGN PATENT DOCUMENTS

| EP | 0497620 | 1/1992 |
| WO | 0176509 | 10/2001 |

*Primary Examiner*—Corrine McDermott
*Assistant Examiner*—William Matthews
(74) *Attorney, Agent, or Firm*—Brinks Hofer Gilson & Lione

(57) ABSTRACT

A barbed medical prosthesis is disclosed in which the barb includes a basal portion comprising a point of union with the substrate of origin (such as a strut), an anchoring portion adapted to embed into tissue, and a stress-dispersing portion located between the basal and anchoring portions. In one embodiment the stress-dispersing portion comprises a helical coil having a free winding that is unattached to the strut from which the barb extends. In another embodiment, the stress-dispersing portion comprises a series of bends or curves formed in the barb proximate to the point of union with the strut. The barb can be mechanically attached and/or soldered to the prosthesis, or integrally formed therefrom. A second barb portion and stress-dispersing portion, may also extend from the basal portion.

20 Claims, 3 Drawing Sheets

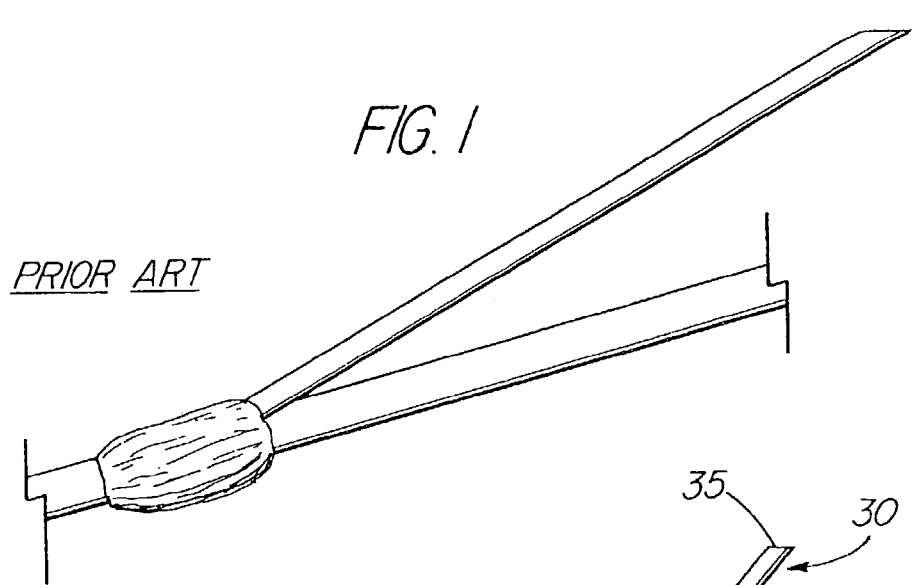
FIG. 1 PRIOR ART
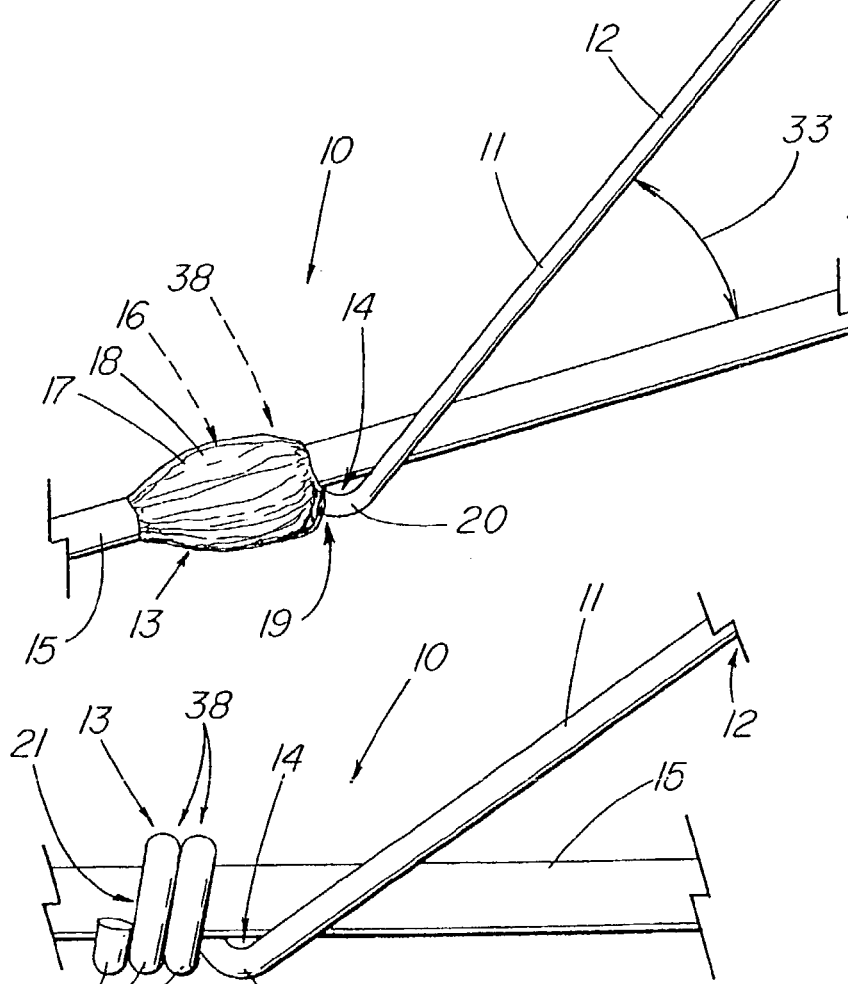
FIG. 2
FIG. 3

FLEXIBLE BARB FOR ANCHORING A PROSTHESIS

CROSS-REFERENCE TO RELATED APPLICATIONS

This application claims priority of provisional application Ser. No. 60/381,046, filed May 16, 2002.

TECHNICAL FIELD

This invention relates to medical devices, more particularly to stents and other prosthetic devices having anchoring barbs.

BACKGROUND OF THE INVENTION

Migration can be a significant problem in the placement of expandable stents and other intraluminal devices, particularly when placed in the vascular system where the prosthesis is subject to the forces of blood flow, especially on the arterial side. Nowhere is the prevention of migration more important and more challenging than when placing a stent graft to repair an abdominal aortic aneursym (AAA) where downstream migration of the device can result in the aneursym no longer being excluded. If the aneurysm is no longer intact or subsequent rupture were to occur, the patient would then face an increased risk of death. Unlike surgically placed grafts which are sutured into place, only the radial forces of the stent would be available to hold the prosthesis into place.

To address the problem of migration, stent graft manufacturers sometimes place a series of barbs or hooks that extend outward from the main body of the prosthesis, typically at its proximal end, either by attaching them to the stent frame with solder or by some other bonding technique, or to the graft material, typically by suturing. It has been observed that sutures attaching barbed stents to the graft material are subject to breakage due in part to the flexibility of the graft material and the considerable pulsatile forces of arterial blood acting on the device. These forces have been known to directly contribute to the detachment between the graft portion and anchoring stent.

It has also been observed that barbs soldered or otherwise attached to the stent frame are subject to fracture, detachment, or other failure, especially when the forces become concentrated at a particular location along the stent graft. Unfortunately, simply making the barbs stronger to prevent fracture can result in increased damage to the anchoring tissue. Furthermore, adding rigidity to any outward-projecting barbs may compromise the ability of the device to be compressed and loaded into a delivery system. The use of multiple barbs can prevent catastrophic migration of the device, especially if there are a very limited number of barb failures. Yet, while a single barb failure should not result in the migration of the device and may not represent a problem clinically, barb fracture or failure is nevertheless currently classified as an adverse event that manufacturers seek to avoid.

One solution to address barb failure was disclosed in U.S. Pat. No. 5,720,776 to Chuter et al., depicted in FIG. 1, where the barb includes both a mechanical attachment, as well as the traditional solder bond. The mechanical attachment comprises a helical winding of the basal portion of the barb around a strut of the stent prior to addition of the solder joint to help protect the solder joint from failure. In addition, the barb is made laterally flexible to help accommodate forces acting at the anchor point. These improvements help ensure that the barb does not readily detach from the stent due to a failure of the solder joint alone. While the combination of both solder and a mechanical means to affix the barb to the stent has proved effective in most respects; however, this area of the barb remains most subject to stresses, such as from cyclic load resulting from the pulsatile action of the implant vessel. What is needed is a barb design that is better able to accommodate or distribute bending and shear stresses in order to further reduce the likelihood of barb failure due to fracture.

SUMMARY OF THE INVENTION

The foregoing problems are solved and a technical advance is achieved in an illustrative barbed prosthesis, such as a stent or stent graft, in which the barb 11 comprises a basal portion that joins the strut of the prosthesis from which the barb extends, and a stress-dispersing region located between the anchoring portion and the basal portion, usually closely adjacent to the basal portion, that is adapted to better distribute stresses and strain caused by forces acting on the barb, thus preventing their concentration at a particular point which would increase the likelihood of barb fracture. As used herein, a 'barb' is defined as an elongate or short structure such as a straight or curvilinear wire, hook, projection, etc., typically including a distal end that includes a sharp edge and/or point, that extends outward from some portion of the prosthesis and is designed to penetrate tissue adjacent to the prosthesis, such as the walls of a vessel, to temporarily or permanently anchor the device at the location of deployment within the body of a patient. The barb can comprise the same material as the prosthesis, such as stainless steel, a superelastic alloy, polymer, etc., or of a different material. The barb may be attached to the prosthesis mechanically, such as being wound or crimped; bonded, such as by solder, an adhesive, or welding; fastened in a manner to allow it to slide along the strut (typically until contacting a stop); or the barb may represent an integral part of the prosthesis. It may be advantageous in particular applications to form the stress-dispersing region in a manner to prevent significant residual stresses in the material. This can be accomplished by the use of methods or materials well known the art.

In one aspect of the present invention, the basal portion and stress-dispersing region comprises a helical coil that is wound around the barb to which it is attached. The windings of the basal portion form a mechanical attachment to which a solder joint or other bonding means is added as a second means of attachment. It should be noted that the present invention may include either means of fixation or attachment of the barb to the strut (or neither in the case of an integral barb) and does not require that both types of fixation be present. One advantage of the mechanical fixation is to provide a backup means of fixation in the event that the solder erodes from contact with bodily fluids.

In the illustrative embodiment, the last or distal winding of the helical coil comprises the stress-dispersing region and is typically of a greater pitch than the windings of the basal portion. It also does not include solder or some other bonding means that affixes it to the strut of the prosthesis, nor does it generally contact the strut. This allows the last winding to remain flexible and thus, accommodate the forces acting upon the anchoring portion of the barb, which is embedded in the adjacent tissue. The majority of the stress load acting on the barb is distributed over the entirety of the large-radius helical bend of the winding to reduce the likelihood of fracture, rather than allowing these forces to concentrate about a single point, typically where the barb first extends from the point of union between the barb and the strut (and solder joint in this particular embodiment). In a related embodiment, the second end of the barb can comprise a second anchoring portion and stress-dispersing region extending oppositely from the basal portion and area of fixation to form a double-ended barb.

In another aspect of the invention, the basal portion of the strut is secured to the strut with a piece of cannula or similar structure that is crimped or bonded in place, such as with the illustrative solder joint. The stress-dispersing region comprises a pair of bends that facilitate lateral flexing of the barb to reduce the risk of fracture. In a related embodiment, the barb extends from the solder joint, then assumes a series of stress-dispersing bends that are proximal to the anchoring portion.

In yet another aspect of the present invention, the stress-dispersing region of the barb comprises a coiled loop bend, U-shaped bend, or other series of bends distal to the point of attachment to add flexibility to the barb, thus reducing bending fatigue and the risk of barb fracture. The barb may include both a coiled loop bend (or other type of bend) and a free helical winding to add further flexibility.

In still yet another aspect of the present invention, the barb integrally formed with the strut, such as by laser cutting a flat sheet or cannula. The stress-dispersing area comprises one or more bends and/or fillets to prevent the concentration of stress in the area immediately adjacent the union between the strut and barb.

BRIEF DESCRIPTION OF THE DRAWING

Embodiments of the present invention will now be described by way of example with reference to the accompanying drawings, in which:

FIG. 1 depicts a side view of a prior art barb soldered to the strut of a stent;

FIG. 2 depicts a side view of the illustrative embodiment of the present stent barb having a stress-dispersing region;

FIG. 3 depicts a side view of the barb of FIG. 2 prior to attachment to the strut;

DETAILED DESCRIPTION

Figure 4:
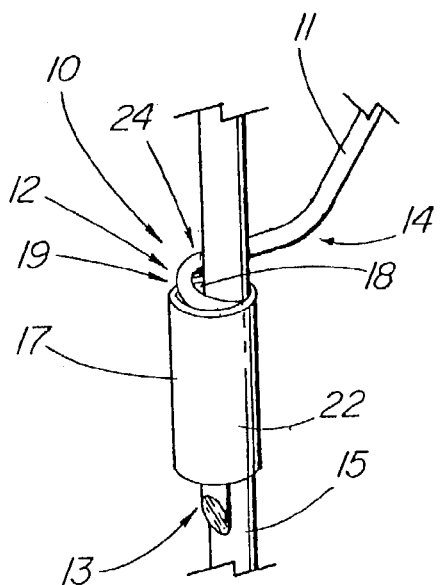
FIG. 4 depicts a side view of an embodiment of the present invention in which the barb is attached to the strut using a piece of cannula.

FIGS. 2–8 depict a medical prosthesis 10, such as a stent, stent graft, valve, vessel occluder, filter, or other intraluminal medical device, that includes one or more barbs 11 that comprise an anchoring portion 12 sized and oriented to engage tissue for the purpose of anchoring the device and preventing the downstream migration thereof; a basal portion 13 located about the physical union between the barb and the strut of the prosthesis 10 to which it is affixed; and a stress-dispersing region that forms a transition between the basal portion 13 and anchoring portion 12 of the barb 11. The stress-dispersing (or stress-reducing) region 14 of the present invention comprises a section of the barb that has been shaped and configured to receive most of the forces acting upon the anchoring portion 12 or moment arm of the barb as it bends and distribute them throughout that region 14, rather than allowing them to be concentrated at a single point or relatively narrow region, such as the point of union 19 between the barb 11 and substrate of origin 15, the substrate of origin 15 typically being a strut 15 of a intraluminal stent or other prosthesis to which the barb 11 is attached. The term 'strut' 15, as defined herein, may encompass a wire, bar, bend, or any portion of the prosthesis from which the barb may emanate, and is not necessarily limited to a strut as traditionally defined in the medical arts, typically meaning a thin section of the metal framework of a self-expanding or balloon expandable stent. For example, the barb may be sewn or otherwise attached directly to graft material or another portion of the prosthesis, or it may be formed integrally with the prosthesis. Additionally, the barb may be slidably affixed to the strut 15 to at least temporarily help relieve stresses about the point of union 19, which is generally defined as that point where the barb extends away from the substrate of origin 15 and/or the means of mechanical attachment 17 or bond 18 between the two.

It should be understood that the delineations between the anchoring portion 12, the stress-dispersing portion 14, and basal portion 13, while primarily functional in nature, are not absolute. The basal portion may represent a well-defined and distinct section of the barb, or merely represent the point of attachment or union with the strut 15 or framework of the prosthesis 10. In addition, the stress-dispersing region 14 may extend sufficiently away from the strut 15 that it also may penetrate adjacent tissue and serve to help anchor the stent. Generally, however, the stress-dispersing region 14 is located proximate to the point of union 19 such that the anchoring portion 12 provides most of the anchoring function.

Although the addition of structure for reducing moment of stress can be placed anywhere along the length of the barb 11, it is most advantageous when located near the base thereof (point of union 19), especially if the stress load is being placed over a significant portion of the barb's length. For example, a series of bends or coils located exclusively at the midpoint of the barb 12 would provide little, if any, stress-relieving value if those bends become imbedded in tissue. In such a situation, the stress moment caused by the torsional and other bending forces acting on the barb would be transferred down toward the barb's base where stress-dispersing structure is lacking.

Figure 8:
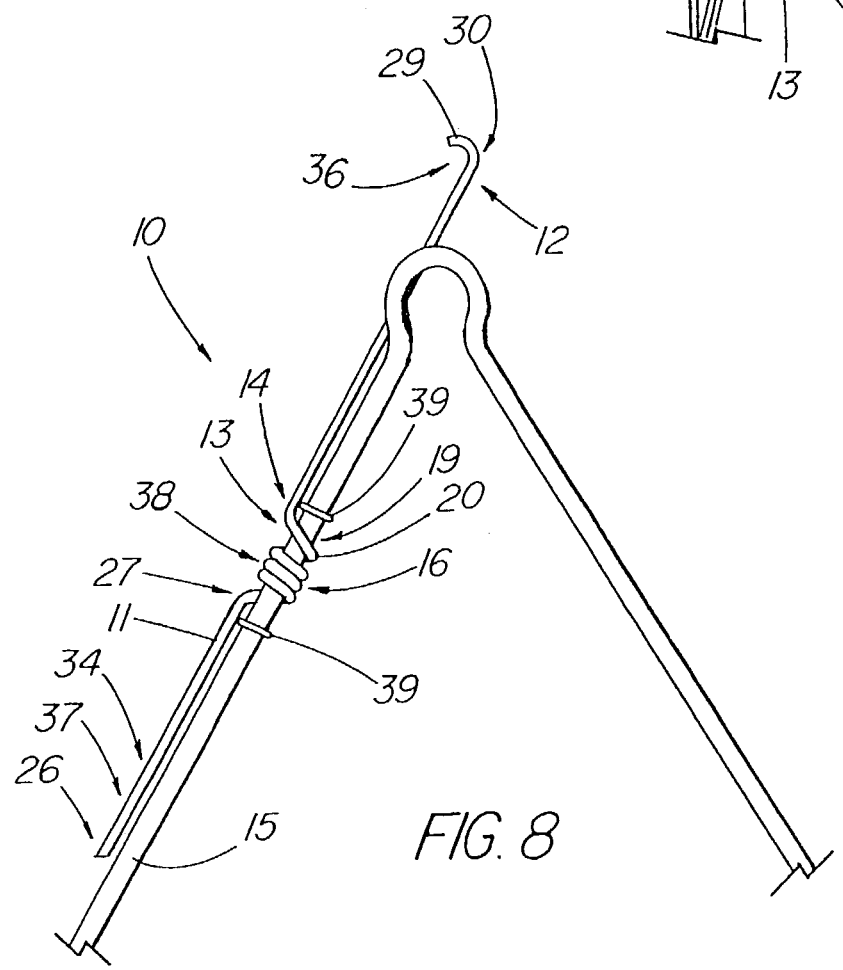
FIG. 8 depicts a side view of an embodiment of the present invention in which the barb includes more than one anchoring portion and associated stress-dispersing region.

FIGS. 2 and 3 depict an illustrative embodiment of the present invention of a type of barb 11 that includes a helical coil 38 that is wound around the strut 15 to which it is attached. The barb 11 in configured to anchor a stent or other prosthesis, such as the suprarenal stent of a endovascular stent graft, such as a ZENITH™ AAA Endovascular Graft (Cook Incorporated) used to treat an abdominal aortic aneurysm (AAA) located in the vicinity of the aortic bifurcation. A series of staggered barbs are affixed to the proximal, suprarenal Z-STENT™ (Cook Inc.) to anchor the stent graft within the proximal neck of the aneurysm being treated and prevent downstream migration of the device which could lead to leakage of blood into the aneurysmal sac. In this particular device, the illustrative barb 11 is designed to orient away from the heart in the direction of aortic blood flow; however, oppositely-oriented barbs may be used in certain other devices intended for aneurysm repair, such as a thoracic stent graft which would be placed in the aortic arch. The orientation of the barb in each of the embodiments of the present invention is determined not only by where the device is placed in the body (i.e., accounting for the direction of blood or fluid flow), but by the type of barb as well, e.g., whether or not the barb includes a hooked end 29, as depicted in FIG. 8. In addition, barbs of different orientation may be used within the same device.

To form the helical coil 38 of the illustrative barb 11 of FIGS. 2–3, a length of 0.008–0.012" diameter wire (such as 0.01" spring stainless steel wire) is either machine wound or hand wound around the strut 15 such that the strut traverses the lumen 21 formed by the helical coil 38, thus forming a mechanical attachment 17 between the barb 11 and strut 15, best shown in FIG. 3. The helical windings 16 of the basal portion 13 have a first pitch 31 in which the windings 16 typically, but not necessarily, lie directly adjacent to one another.

Returning to FIG. 2, low-temperature silver solder, or some other bonding agent, is applied to the windings 16 of the basal portion 13 to form a permanent bond 18 that reinforces the mechanical attachment of the helical windings and secures the barb longitudinally along the strut 15. Besides the illustrative solder joint 18, alternative methods of forming a permanent bond 18 include welding or the use of adhesives. As depicted in FIGS. 2–3, helical coil 38 includes a winding 20 distal to those of the basal portion 13 and the point of union 19 between the barb 11 and strut. Referred to herein as the free winding 20 because it neither is soldered to the strut, or is generally in contact with the strut, except perhaps in an insignificant or incidental way, the free winding comprises the stress-dispersing region 14 of the barb. It should be noted that the free winding 20 does not necessarily completely encircle the substrate of origin or strut and may only constitute a partial winding. The free winding 20 is of a second pitch 32 that is typically greater (more loosely wound) than the first pitch 31 of windings 16 of the basal portion 13, although it is not essential that the basal winding 16 be closely adjacent to one another as depicted.

By enlarging the radius of the winding 20, such that it is no longer contacting the strut 15, the bending stress is more evenly distributed than would be the case if there were a tighter winding (with less pitch), thereby increasing the fatigue life of the barb. Furthermore, the fact that the free winding 20 of the barb is not affixed to, nor is in contact with, the strut 15 allows the entire free winding 20 to freely flex and distribute most the bending forces over its entire length. This helps prevent the concentration of torsional and bending stresses at the point of union 19 where the barb 11 extends out from the solder joint 18, typically the most common location of barb fracture in the prior art barb illustrated in FIG. 1.

The anchoring portion 12 of the illustrative barb 11 of FIG. 2 comprises a straight section extending from the stress-dispersing portion such that the overall barb 11 length is about 5 mm, the typical range being 3–8 mm, depending on the stent used. The barb 11 extends at an angle 33 from the strut to facilitate the capture of anchoring tissue, the preferred post-deployment angle 33 being about 20–50°, e.g. 35°, in the illustrative embodiment used to anchor the suprarenal stent of a AAA endovascular graft. Due to plastic deformation that may occur during loading of the device into a delivery system, such as a top cap, this angle may be initially formed at a somewhat larger angle 33 (i.e., 40–80°).

The distal end 30 of the barb includes a bevel 35 to facilitate penetration of the vessel wall, with the sharp point being oriented toward the strut 15. The particular barb angle 33 and bevel 35 orientation are selected, in part, to ensure that the device 10 can be compressed to a smaller configuration and loaded into the top cap (not shown) of a delivery system and successful deployed therefrom such that the barb 11 does not deform or become caught within the cap, while still being able to resiliently extend outward to its expanded configuration and effectively engage tissue.

FIG. 4 depicts an alternative embodiment of the present invention in which a short piece of metal cannula 22 is used as the mechanical attachment 17 to affix the barb 11 to the strut 15 of the intraluminal prosthesis 10. The basal section 13 of the barb 11 is secured against the strut 15 by the cannula 22, which is crimped over the barb and/or affixed using a solder joint 18 or some other means of fixation. At the point of union 19 of the barb 11 as it exits the region of attachment 17, the barb 11 assumes a series of bends or curves 24 that comprise the stress-dispersing region 14, after which the anchoring portion 12 extends outward at the appropriate angle from the strut 15. Alternatively, the cannula 22 can be used in combination with another type of mechanical attachment 17, such as the helical windings 16 of FIG. 3 in which the last winding 20 would comprise the stress-dispersing region 14.

Figure 5:
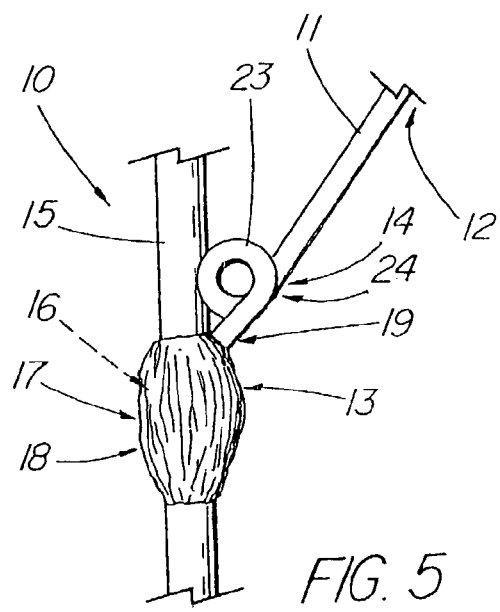
FIGS. 5–5b each depict a side view of an embodiment of the present invention in which the stress-dispersing region of the barb includes a coiled bend.
Figure 5A:
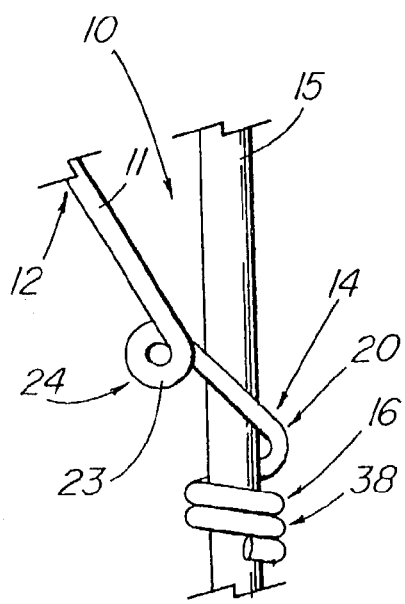
Figure 5B:
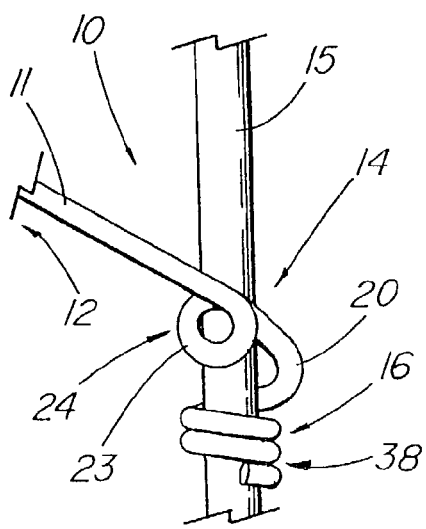
Figure 6:
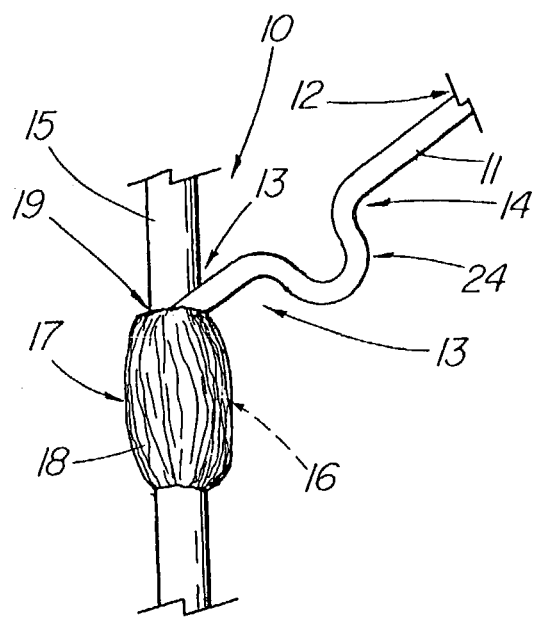
FIG. 6 depicts a side view of an embodiment of the present invention in which the stress-dispersing region of the barb comprises a complex bend.

FIGS. 5–6 depict alternative embodiments of stress-dispersing regions 14 of the barb 11 of the present invention which can be used with a variety of basal portion 13 configurations and types of attachments 17. In the embodiments of FIGS. 5, 5a, and 5b, stress-dispersing region 14 comprises a complete coiled loop 23 whereby the wire makes approximately a one and quarter turn between the basal portion 13 the anchoring portion 12 of the barb 11. The illustrative loop 23 provides a known mechanical advantage that it increases the range of flexibility at that bend, as evidenced by its use in certain medical devices, such as stents, and other devices with sharp bends (e.g., safety pins). Although the tighter-radius bends in general, can provide a site having an increased risk of fracture, this may be more than offset by the added flexibility of the barb, depending on the configuration. FIGS. 5a and 5b depict embodiments that include both the free winding 20 as depicted in the embodiments of FIGS. 2–3, as well as a coiled loop 23 that is located adjacent to the free winding 20. In the embodiment of FIG. 5a, the coil is discrete from the free winding 20, wherein in the embodiment of FIG. 5b, a portion of the coiled loop 23 originates from the free winding 20 such that they are essentially contiguous with one another. The combination of the coiled loop 23 and free winding 20 form a stress-dispersing region 14 having different flexibility characteristics that may be desirous in a particular application.

The embodiment of FIG. 6 includes a generally U-shaped bend 24 that comprises the stress-dispersing region 14. The embodiments of FIGS. 5–6 are merely exemplary of the numerous configurations of bends 24 that can be utilized to redistribute bending stresses and reduce the risk of fracture. These and other undisclosed bends may used in combination within the stress-dispersing region 14 to further distribute the stress load of the implanted barb 11. Like the embodiments of FIGS. 5a–5b, the bends 24 may be combined with a free helical winding 20 for added flexibility.

Figure 7:
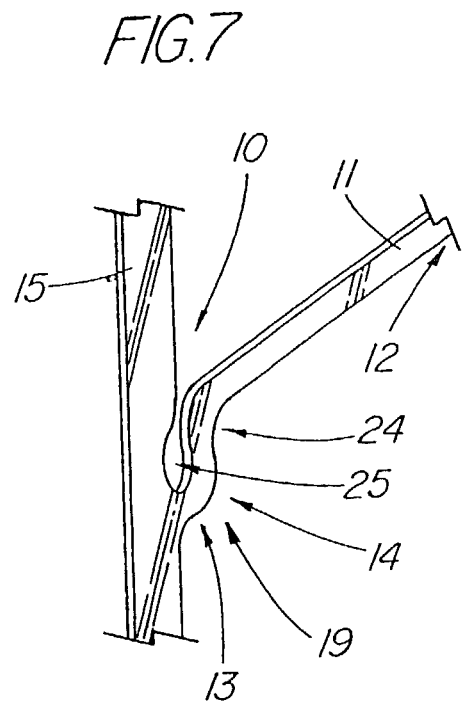
FIG. 7 depicts a side view of an embodiment of the present invention in which the barb in integral with the strut of the stent.

FIG. 7 depicts an integrally formed barb 11 in which the barbed prosthesis 10 is partially or completely formed from a sheet of metal or other material, such as by laser cutting, eliminating the need for an separate attachment mechanism 17. The basal section 13 of the barb 11 basically comprises the point of union 19 between the strut portion 15 and the barb portion 11 from which it extends. In the illustrative embodiment, the stress-dispersing region 14 comprises a series of bends 24, as well as a fillet 25 at the union 19 with the strut to further reduce stress concentration.

FIG. 8 depicts an embodiment of the present invention in which the prosthesis 10 includes a doubled-ended barb 11 having a first barb portion 36 that includes a first anchoring portion 12 and associated first stress-dispersing portion 14, and a second barb portion 37 that includes a second anchoring portion 26 and associated second stress-dispersing portion 27, all extending from a single basal portion 13, which in the illustrative embodiment, comprises a helical coil 38 similar to that depicted in FIG. 3. Both the first free winding 20 extending from the first barb portion 36 and the second free winding 27 extending oppositely from the basal portion 13 are unattached to the strut 15 and free to flex and distribute any bending stresses therealong. Additionally, FIG. 8 also illustrates an alternative attachment means between the barb 11 and strut 15, wherein rather than a mechanical attachment 17 or bonding attachment 18, the helical coil 38 is allowed to slide along the strut 15, which may reduce the stress moment along the barb 11 in certain situations. To prevent the barb from sliding too far in either direction, a pair of stops 39, such as beads of solder, welded structure, burs formed in the strut 15, etc. are placed at either end of the basal portion 13. In the illustrative double barb 11, the first barb portion 36 includes a terminal hook 29 for anchoring the device to prevent migration due to blood or fluid flow, while the oppositely oriented second barb portion 37 includes a straight distal end 34. Alternatively, the exemplary double-ended barb 11 can be modified to include other disclosed configurations of the basal, stress-dispersing or anchoring portions or regions 12, 13, 14 of the barb 11 or any appropriate means of attachment to the strut 15.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27th edition.

What is claimed is:

1. An intraluminal medical device configured for deployment within the body of a patient, comprising:
   at least one barb comprising a base, an anchoring portion configured to penetrate tissue adjacent the prosthesis, and a non-linear stress-dispersing region spaced apart from and located between the base and the anchoring portion; and
   at least one strut joined to the base such that a point of union between the base and the at least one strut is formed, and
   a non-linear stress-dispersing region disposed spaced from and proximate to the point of union;
   where the point of union comprises a helical coil and the non-linear stress-dispersing region comprises at least one separate free winding, and where the at least one free winding is configured to flex in response to a stress load placed on the anchoring portion of the barb.

2. The barbed prosthesis of claim 1, where the helical coil comprises windings having a first pitch, and the free winding has a second pitch that is greater than the first pitch.

3. A barbed prosthesis configured for deployment within the body of a patient, comprising:
   at least one strut;
   at least one barb joined to the at least one strut to form a point of union between the barb and the strut;
   wherein the barb comprises an anchoring portion spaced apart from the point of union and configured to penetrate tissue adjacent the prosthesis; and
   a non-linear stress-dispersing region disposed between and spaced apart from the point of union and the anchoring portion, where the non-linear stress-dispersing region is more proximate the point of union than the anchoring portion.

4. The prosthesis of claim 3, where the barb is joined to the at least one strut by mechanical attachment means, by bonding means, or a combination of mechanical attachment and bonding means.

5. The prosthesis of claim 3, where the non-linear stress-dispersing region comprises at least one bend spaced apart from the point of union.

6. The prosthesis of claim 3, where the non-linear stress-dispersing region comprises a series of bends spaced apart from the point of union.

7. The prosthesis of claim 3, where the non-linear stress-dispersing region extends away from the at least one strut.

8. The prosthesis of claim 3, where the point of union comprises a helical coil formed about the strut wherein the coil comprises a series of windings having a first pitch.

9. The prosthesis of claim 8, where the stress-dispersing region comprises at least one separate free winding extending distally and spaced apart from the windings of the point of union, where the free winding has a second pitch that is greater than the first pitch.

10. The prosthesis of claim 9, where the free winding comprises a partial winding.

11. The prosthesis of claim 3, where the non-linear stress-dispersing region is configured to flex in response to a stress load placed on the anchoring portion of the barb.

12. An intraluminal medical device configured for deployment within the body of a patient, comprising:
   at least one stent having a one or more struts;
   at least one barb joined to at least one strut to form a point of union between the barb and the strut;
   wherein the barb comprises an anchoring portion spaced apart from the point of union and configured to penetrate tissue adjacent the stent; and a non-linear stress-dispersing region disposed between and spaced apart from the point of union and the anchoring portion, where the non-linear stress-dispersing region is more proximate the point of union than the anchoring portion.

13. The prosthesis of claim 12, where the barb is joined to the strut by mechanical attachment means, by bonding means, or a combination of mechanical attachment and bonding means.

14. The prosthesis of claim 12, where the non-linear stress-dispersing region comprises at least one bend spaced apart from the point of union.

15. The prosthesis of claim 12, where the non-linear stress-dispersing region comprises a series of bends spaced apart from the point of union.

16. The prosthesis of claim 12, where the non-linear stress-dispersing region extends away from the strut.

17. The prosthesis of claim 12, where the point of union comprises a helical coil formed about the strut wherein the coil comprises a series of windings having a first pitch.

18. The prosthesis of claim 17, where the stress-dispersing region comprises at least one separate free winding extending distally and spaced apart from the windings of the point of union, where the free winding has a second pitch that is greater than the first pitch.

19. The prosthesis of claim 18, where the free winding comprises a partial winding.

20. The prosthesis of claim 12, where the non-linear stress-dispersing region is configured to flex in response to a stress load placed on the anchoring portion of the barb.

* * * * *